United States Patent [19]

Bieri

[11] Patent Number: 5,240,861
[45] Date of Patent: Aug. 31, 1993

[54] DEVICE AND PROCESS FOR CONCENTRATING BIOLOGIC SPECIMENS IN LIQUID FORM

[75] Inventor: Daniel Y. Bieri, Paris, France

[73] Assignee: Spectrum Medical Industries, Inc., Los Angeles, Calif.

[21] Appl. No.: 225,738

[22] Filed: Jul. 29, 1988

[51] Int. Cl.$^5$ .............................................. G01N 1/18
[52] U.S. Cl. .................................... 436/178; 436/63; 436/807; 436/809; 422/58; 422/101
[58] Field of Search ................ 436/178, 807, 809, 63; 422/58, 101; 435/302, 311; 206/221, 219; 220/254

[56] References Cited

U.S. PATENT DOCUMENTS

| | | | |
|---|---|---|---|
| 3,715,189 | 2/1973 | Nighohossian et al. | 206/219 |
| 4,208,187 | 6/1980 | Givner | 422/59 |
| 4,210,623 | 6/1980 | Breno et al. | 422/101 |
| 4,550,825 | 11/1985 | Sutryn et al. | 206/219 |
| 4,858,759 | 8/1989 | Mauthe et al. | 206/219 |

OTHER PUBLICATIONS

Fischer Scientific 81 Complete Chemical Catalog, p. 324.

*Primary Examiner*—James C. Housel
*Assistant Examiner*—Lyle A. Alexander
*Attorney, Agent, or Firm*—Edgar W. Averill, Jr.

[57] ABSTRACT

A device for concentrating liquid specimens and the process of using the device. The device has a receptacle containing a membrane. The sample to be concentrated is placed in the receptacle on the upper surface of the membrane. A piston is then screwed down toward the upper surface of the membrane increasing the pressure above the membrane. The process for using the device involves supporting the device at a small angle from the vertical so that once the specimen has been concentrated to a given volume, the tilted membrane is exposed allowing air to reach the membrane and equalizing the pressure thereby rapidly decreasing any further concentration.

20 Claims, 2 Drawing Sheets

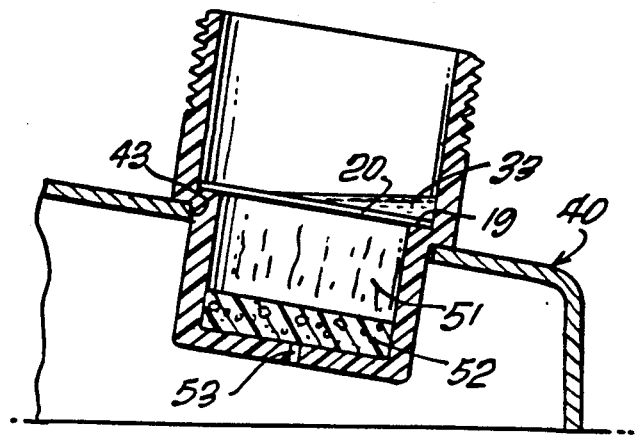
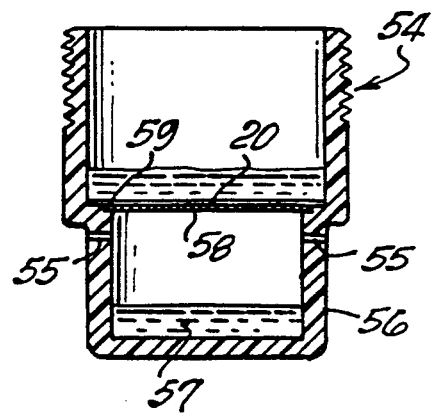
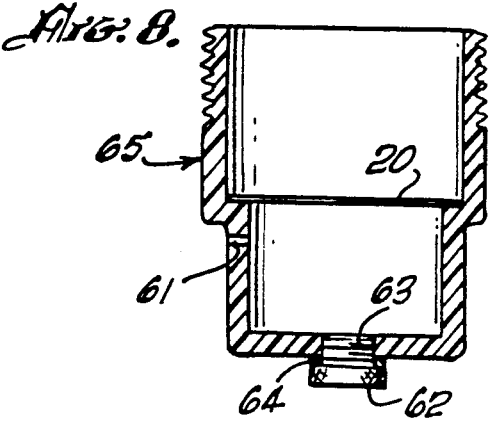
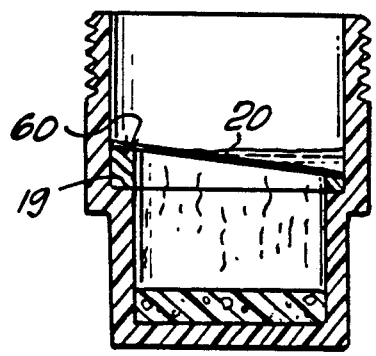

DEVICE AND PROCESS FOR CONCENTRATING BIOLOGIC SPECIMENS IN LIQUID FORM

BACKGROUND OF THE INVENTION

The field of the invention is laboratory apparatus and the invention relates more particularly to devices for concentrating small liquid specimens.

One disposable device is shown in U.S. Pat. No. 3,187,379 assigned to Amicon Corporation wherein a liquid specimen is placed in a chamber which has a membrane along one side. The membrane has an absorbent material pressed against its inner surface and the specimen is poured into a chamber against its outer surface. The specimen tends to flow through the membrane into the absorbent material. In one form, an impervious sheet is placed near the lower portion of the chamber to retain a certain minimum amount of liquid in the chamber no matter how long the sample is left in the chamber. While the Amicon device has found widespread use, it has several shortcomings. First, the time required for concentration to be completed can be quite slow, often taking up to one day. Secondly, the sample is open to the atmosphere and if left overnight, a portion of the sample can be lost. Because of the design of the Amicon device and its use of an impervious layer, the sample is in contact with only a very small amount of the membrane as it nears the level of the impervious layer.

To reduce concentration time, the centrifugation of a sample over a membrane is sometimes used to increase the flow through the membrane. Centrifugation requires additional equipment and provides limited control over final sample volume.

SUMMARY OF THE INVENTION

It is an object of the present invention to provide a device for concentrating specimens in liquid form which may be rapidly carried out and which may retain a predetermined volume of concentrated liquid.

The present invention is for a device for concentrating specimens in liquid form. The device consists of a cylindrical receptacle upon which a removable lid is threaded. The cylindrical receptacle has an inner cavity, including inner sidewalls, and at least a portion of the inner sidewalls has a smooth, cylindrical inner surface for contact with a piston. A removable cover has threads which mate with threads on the receptacle. The cover has a closed, air-tight top and includes a cylindrical piston which forms an air-tight seal with the inner surface of the receptacle. A membrane is held within the inner cavity of the receptacle in a leak-proof manner and is positioned below the lower-most portion of the piston of the cover. The membrane has an upper surface facing in the direction of the piston and a lower surface facing in the direction of the bottom of the body. As the cap is screwed on the body, the piston moves downwardly and increases the pressure above the membrane. In order to have the sample concentrated to a predetermined volume, a rack may be provided which holds the device at an angle typically up to 30° with respect to the horizontal. The sample on the upper surface of the membrane is reduced in size as a portion of the liquid passes through the membrane. Once the liquid level uncovers the upper corner of the membrane, the gas above the membrane can pass through the membrane thereby equalizing the pressure on both sides of the membrane. This reduces any significant flow through the membrane. Preferably, the membrane is sealed on a step formed in the inner surface of the receptacle.

BRIEF DESCRIPTION OF THE DRAWINGS

FIG. 4 is a cross-sectional view of one of the devices shown in FIG. 2.

FIG. 5 is a cross-sectional view of an alternate form of the body of the device of FIG. 1.

FIG. 6 is a cross-sectional view of an alternate embodiment of the body of the device of FIG. 1.

FIG. 7 is a perspective view of a support ring of the body of FIG. 6.

FIG. 8 is a cross-sectional view of an alternate embodiment of the body of the device of FIG. 1.

DESCRIPTION OF THE PREFERRED EMBODIMENTS

Figure 1:
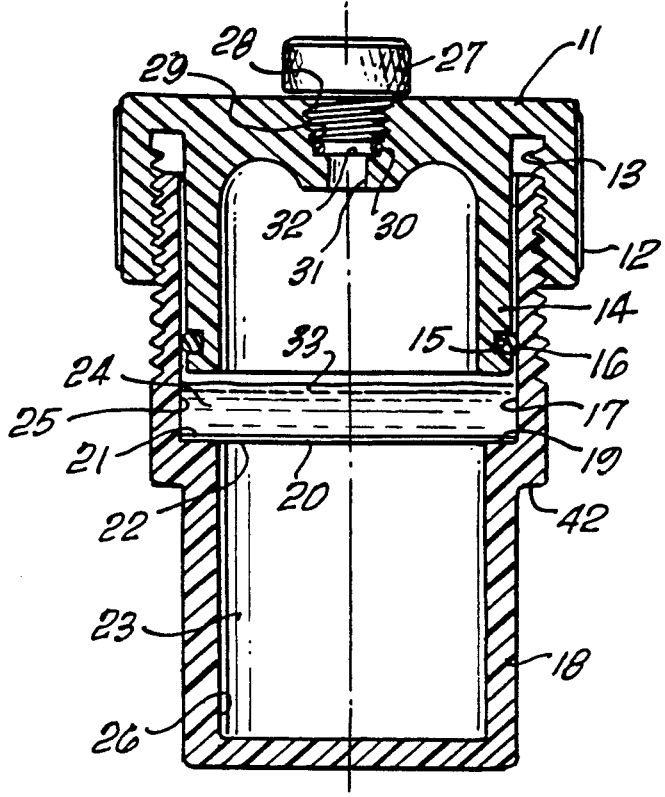
FIG. 1 is a cross-sectional view of the device for concentrating liquid specimens of the present invention.

The device for concentrating liquid specimens is shown in cross-sectional view in FIG. 1 and indicated generally by reference character 10. Device 10 has a cover 11 with a downwardly extending threaded ring 12 which include thread means 13 on the inner surface thereof. Cover 11 has a cylindrical piston 14 which includes groove 15 which holds an O-ring 16.

Piston 14 of cover 11 forms an air-tight fit with the inner surface 17 of generally cylindrical receptacle 18. Receptacle 18 has a flat step 19 to which a membrane 20 is sealed. Membrane 20 has an upper surface 21 and a lower surface 22. Receptacle 18 has an inner cavity comprising a lower portion 23 below membrane 20 and an upper cavity 24 above membrane 20. The inner sidewall of upper cavity 24 is indicated by reference character 25 and the inner sidewall of lower cavity 23 is indicated by reference character 26.

Cover 11 has a cap 27 which has threads 28 which meet with threads 29 formed in cover 11. An O-ring 30 seats against a flat step 32 formed at the upper edge of opening 31. Cap 27 may be removed to assist in the removal of cover 11 which would otherwise form a partial vacuum as it is removed. Alternatively, the sample may be either introduced or withdrawn through opening 31 once cap 27 has been removed. Of course, cap 27 is tightened in a closed position to form an air-tight seal with respect to cover 11.

In use, a liquid specimen, indicated by reference character 33 in FIG. 1, is placed on the upper surface 21 of membrane 20. Cap 27 is tightened in cover 11 and cover 11 is then screwed downwardly to the position shown in FIG. 1. This increases the pressure in the upper cavity 24 thereby increasing the pressure drop across membrane 20. This increases the flow of a portion of specimen 33 through membrane 20. Membrane 20 is a membrane which has small pores through it such as a cellulosic membrane. Such membranes are widely used for ultrafiltration and other separation procedures. Such membranes permit the passage of smaller molecules while retaining larger molecules above the membrane. In this manner, a liquid sample may be concentrated typically by having a portion of the water removed therefrom.

Figure 2:
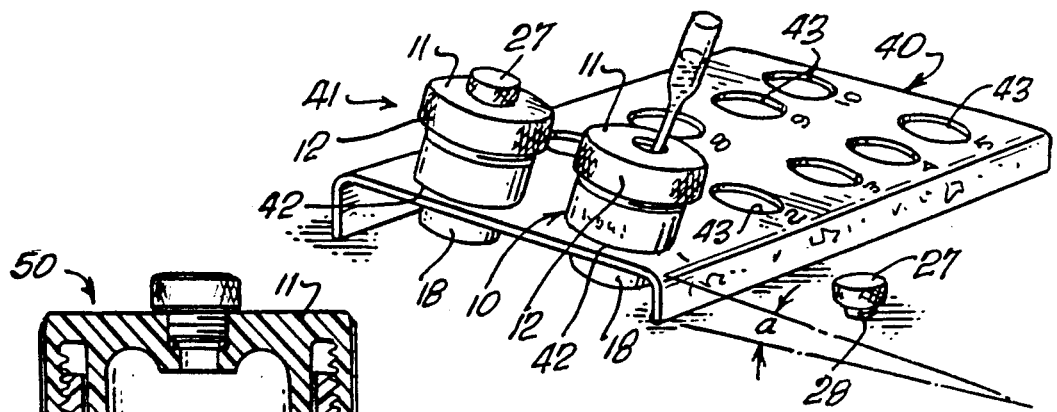
FIG. 2 is a perspective view of a pair of devices of FIG. 1 held at an angle in a rack.

In order to prevent complete loss of the sample and to provide a concentrated sample with a predetermined volume, a rack has been provided as shown in FIG. 2 of the drawings. The rack is indicated by reference character 40, and rack 40 contains two concentrating devices 10 and 41. Both of these devices are identical and each has a step 42, shown in FIG. 1, which rests on the upper surface of rack 40. Rack 40 has a plurality of holes 43 which are slightly larger than the lower portion 44 of generally cylindrical receptacle 18. The upper surface of rack 40 is held at an angle indicated by reference character "a" in FIG. 2 and this angle should be between about 0° and 30°. An angle of about 15° has provided excellent results. As shown best in FIG. 4 of the drawings, when the liquid sample is reduced in size an amount so that the surface of the sample recedes below a portion of the upper surface 21 of membrane 20, this permits gas to flow through the membrane thereby equalizing the pressure o both sides of the membrane and essentially stopping further concentration of the sample.

Figure 3:
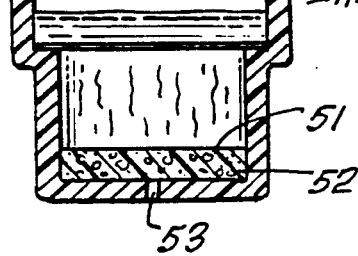
FIG. 3 is a cross-sectional view of an alternate embodiment of device for concentrating liquid specimens of FIG. 1.

An alternate embodiment of the device for concentrating liquid specimens is shown in FIG. 3 and indicated by reference character 50. This device has the same cover 11, but further includes a pad 51 which is made from an absorbent material which assists in drawing liquid through the membrane. Pad 51 may be, for instance, made from cellulosic fibers or other absorbent material. Preferably, pad 51 is held against the lower surface 22 of membrane 20 by an elastic sponge 52. Also, to prevent a pressure buildup below membrane 20, a vent 53 may be drilled to the base of generally cylindrical receptacle 18.

For some tests, it is desirable to maintain a sample of the liquid which is passed through membrane 20 and a device capable of doing this is shown in FIG. 5 and indicated by reference character 54. This device conforms closely to the generally cylindrical receptacle 18 of FIG. 1 but differs in two respects. First, a plurality of notches 55 is formed in receptacle 56 so that the lower portion of receptacle 56 can be separated at the notches to permit access to the liquid sample 57 which is passed through membrane 20. Secondly, a membrane support screen 58 is sealed in a step 59 in receptacle 56. This permits increased pressure against the membrane. Alternatively, a threaded plug could be placed in the bottom of the receptacle. The plug may be removed to permit recovery of the sample filtrate.

An alternate means of holding the membrane at a small angle is shown in FIG. 6 where membrane 20 is held on an angled ring 60 which rests on step 19. In this way, the device can be held in a vertical manner while the volume of the sample can be controlled, as described above, with respect to the use of rack 40. Ring 60 is shown in perspective view in FIG. 7.

The use of the device of the present invention significantly decreases the time required to concentrate samples in solution. No centrifugation is necessary, and the process of using the device is very simple. The amount of pressure formed above the membrane is limited by the limited amount that the cover 11 may be screwed down on the cylindrical receptacle 18. The further use of an absorbent pad tends to further increase the flow rate through the membrane. Furthermore, the sample is retained in a covered configuration. Even if the sample is left overnight, it will not be able to evaporate or otherwise become contaminated since it is closed below piston 14.

By using a membrane having a diameter of 40 millimeters, a sample having a volume of about 6 milliliters is appropriately concentrated.

An alternate embodiment of concentrator is shown in cross-sectional side view in FIG. 8. The concentrator body 65 has a vent 61 formed below the membrane 20. This retains the pressure on the undersurface of membrane 20 at atmospheric pressure and assures a pressure gradient across the membrane after the piston has been screwed or otherwise moved downwardly above the membrane. Also, a threaded cap 62 is placed in a threaded opening 63 in the bottom of body 65. An O-ring 64 is used to assure that there is no leakage of liquid filtrate. By removing threaded cap 62 after the filtration is complete, a sample of the filtrate may be obtained.

The concentrator of the present invention is preferably fabricated from a polymer capable of being sterilized, although other materials of construction could be used. The choice of materials of construction is related to the use to which the device is put.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. A device for concentrating liquid specimens, said device comprising:
   a generally cylindrical receptacle having an open top, said receptacle having an inner cavity including inner side walls, at least a portion of said inner side walls having a smooth cylindrical inner surface;
   a cover having a closed, air-tight top, and said cover having a cylindrical position which forms an airtight seal with the smooth cylindrical inner surface of the generally cylindrical receptacle;
   means for moving said cylindrical piston downwardly; and
   a semi-permeable membrane held within said inner cavity and sealed to the inner cavity in a manner so that no material may pass between the membrane and the inner cavity, said semi-permeable membrane being positioned below the innermost position of the cylindrical piston of the cover, and said semi-permeable membrane having an upper surface facing in the direction of the open top of the generally cylindrical receptacle and a lower surface facing away from the upper surface, whereby when a liquid specimen is placed in the inner cavity of the generally cylindrical receptacle on the upper surface of the semi-permeable membrane and the cover is moved downwardly on the receptacle, the pressure on the liquid specimen will be increased with respect to the pressure on the lower surface of the semi-permeable membrane and the liquid specimen will have an increased tendency to pass through the semi-permeable membrane.

2. The device for concentrating liquid specimens of claim 1 further including O-ring means held in a groove on the outer surface of the cylindrical piston.

3. The device for concentrating liquid specimens of claim 1 wherein the means for moving the cylindrical piston downwardly comprises turning the cover with respect to the generally cylindrical receptacle and wherein there are thread means on the generally cylindrical receptacle positioned on the outer surface of the generally cylindrical receptacle and the cover has an outer ring having threads on the inner surface thereof and the inner piston is supported by the closed top of the cover.

4. The device for concentrating liquid specimens of claim 1 wherein the inner cavity of the generally cylindrical receptacle has a lower portion and an upper portion, and the lower portion has a smaller inside diameter than the inside diameter of the upper portion and the intersection of the lower portion, and the upper portion has a flat step and said semi-permeable membrane is sealed to said flat step.

5. The device for concentrating liquid specimens of claim 1 further including an absorbent pad held against the lower surface of the semi-permeable membrane, said absorbent pad having an upper surface and a lower surface and the upper surface thereof being adjacent the lower surface of the semi-permeable membrane.

6. The device for concentrating liquid specimens of claim 5 further including an elastic pad positioned against the lower surface of the absorbent pad.

7. The device for concentrating liquid specimens of claim 1 wherein said cover has a removable cap for introducing a sample through said cover into the inner cavity of the generally cylindrical receptacle when the cover is placed on said receptacle, said removable cap forming an air-tight seal with said cover when said cap is placed on the cover.

8. The device for concentrating liquid specimens of claim 7 wherein said air-tight seal is formed by an O-ring positioned between said cover and said cap.

9. The device for concentrating liquid specimens of claim 1 further including a vent opening in said generally cylindrical receptacle in a portion thereof below the lower surface of the semi-permeable membrane.

10. The device for concentrating liquid specimens of claim 1 further including a break-away notch formed in said generally cylindrical receptacle below the semi-permeable membrane.

11. A device for concentrating liquid specimens, said device comprising:
a generally cylindrical receptacle having an open top having threads formed along the outer surface adjacent the open top, said generally cylindrical receptacle having an inner cavity including inner side walls, at least a portion of said inner side walls having a smooth cylindrical inner surface;
a cover having an annular lip having threads on the inner surface thereof which mate with the threads on the generally cylindrical receptacle, said cover having a closed, air-tight top, and said cover having a cylindrical piston held by said top, which piston forms an air-tight seal with the smooth cylindrical inner surface of the generally cylindrical receptacle; and
a semi-permeable membrane held within said inner cavity and sealed to the inner cavity in a manner so that no material may pass between the membrane and the inner cavity, said semi-permeable membrane being positioned below the innermost position of the cylindrical piston of the cover, and said semi-permeable membrane having an upper surface facing in the direction of the open top of the generally cylindrical receptacle and a lower surface facing away from the upper surface, whereby when a liquid specimen is placed in the inner cavity of the generally cylindrical receptacle on the upper surface of the semi-permeable membrane and the cover is threadably inserted on the receptacle, the pressure on the liquid specimen will be increased with respect to the pressure on the lower surface of the semi-permeable membrane and the liquid specimen will have an increased tendency to pass through the semi-permeable membrane.

12. The device for concentrating liquid specimens of claim 11 wherein the inner cavity of the generally cylindrical receptacle has a lower portion and an upper portion and the lower portion has a smaller inside diameter than the inside diameter of the upper portion and the intersection of the lower portion and the upper portion has a flat step and said semi-permeable membrane is sealed to said flat step.

13. The device for concentrating liquid specimens of claim 11 further including an absorbent pad held against the lower surface of the semi-permeable membrane, said absorbent pad having an upper surface and a lower surface and the upper surface thereof being adjacent the lower surface of the semi-permeable membrane.

14. The device for concentrating liquid specimens of claim 13 further including an elastic pad positioned against the lower surface of the absorbent pad.

15. The device for concentrating liquid specimens of claim 11 wherein said cover has a removable cap for introducing a sample through said cover into the inner cavity of the generally cylindrical receptacle when the cover is placed on said receptacle, said removable cap forming an air-tight seal with said cover when said cap is placed on the cover.

16. The device for concentrating liquid specimens of claim 15 wherein said air-tight seal is formed by an O-ring positioned between said cover and said cap.

17. The device for concentrating liquid specimens of claim 11 further including a vent opening in said generally cylindrical receptacle in, a portion thereof below the lower surface of the semi-permeable membrane.

18. The device for concentrating liquid specimens of claim 11 further including a break-away notch formed in said generally cylindrical receptacle below the semi-permeable membrane.

19. A process for concentrating a liquid sample in a device having a generally cylindrical receptacle having a longitudinal axis and having a semi-permeable membrane sealed to a flat step along the interior surface of said receptacle, said flat step being perpendicular to the longitudinal axis and said device having a threaded cap supporting a piston which fits in an air-tight manner against the interior surface of the receptacle so that the threading of the cap on the receptacle increases the pressure above said semi-permeable membrane said process comprising the steps of:
placing a liquid sample in said cylindrical receptacle onto said semi-permeable membrane;
inserting the piston into said cylindrical receptacle;
screwing the cap downwardly onto said cylindrical receptacle thereby depressing the piston toward said semi-permeable membrane;
placing said cylindrical receptacle into a holder which retains the flat step of said cylindrical receptacle at an angle of between 0° and 30° degrees with respect to the horizontal; and
retaining said cylindrical receptacle at said angle for a time sufficient for the inner contents to reach equilibrium.

20. A process for concentrating a liquid sample in a device having a cylindrical receptacle having a longitudinal axis and having a semi-permeable membrane sealingly affixed to a flat step along the interior surface of said receptacle, said flat step being at an angle of from 0° to 30° with respect to the horizontal and said device having a threaded cap supporting a piston which fits in an air-tight manner in the interior surface of the receptacle so that the threading of the cap on the receptacle increases the pressure above said semi-permeable membrane, said process comprising the steps of:

placing a liquid sample in said cylindrical receptacle onto said semi-permeable membrane;

inserting the piston into said cylindrical receptacle;

screwing the cap downwardly onto said cylindrical receptacle thereby depressing the piston toward said semi-permeable membrane;

placing said cylindrical receptacle onto a flat, horizontal surface thereby holding said semi-permeable membrane at an angle of between 0° and 30° degrees with respect to the horizontal; and retaining said cylindrical receptacle on said flat surface for a time sufficient for the inner contents to reach equilibrium.

* * * * *